(12) United States Patent
Ng et al.

(10) Patent No.: US 10,132,752 B2
(45) Date of Patent: Nov. 20, 2018

(54) HAND-HELD LASER BIOSENSOR

(71) Applicant: The United States of America as represented by the Secretary of the Navy, Washington, DC (US)

(72) Inventors: Kin Chiu Ng, Fresno, CA (US); Subrata Sanyal, Eastvale, CA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/712,122

(22) Filed: Sep. 21, 2017

(65) Prior Publication Data

US 2018/0217061 A1 Aug. 2, 2018

Related U.S. Application Data

(60) Provisional application No. 62/451,243, filed on Jan. 27, 2017.

(51) Int. Cl.
*G01N 21/25* (2006.01)
*G01N 21/64* (2006.01)
(Continued)

(52) U.S. Cl.
CPC ..... *G01N 21/6402* (2013.01); *G01N 21/3103* (2013.01); *G01N 21/6458* (2013.01);
(Continued)

(58) Field of Classification Search
CPC ...... G01J 3/02; G01J 3/00; G01J 3/44; G01N 21/65; G01N 21/64; G01N 21/645; G01N 2021/64

See application file for complete search history.

(56) References Cited

U.S. PATENT DOCUMENTS 4,151,415 A * 4/1979 Lipke ..................... G01S 17/89
250/333
5,085,673 A 2/1992 Bentley et al.
(Continued)

FOREIGN PATENT DOCUMENTS

CN 104730040 6/2015
WO WO 2002/061405 8/2002

OTHER PUBLICATIONS

Eastcom, Pergam Technical Services, "Laser Methane Mini", retrieved on Jun. 23, 2016 from http://www.eastcomassoc.com/Eastcom%20Web%20Site%20Brochures/LMm_G_Eastcom%20LowRes.pdf.
(Continued)

*Primary Examiner* — Abdullahi Nur
(74) *Attorney, Agent, or Firm* — Christopher A. Monsey

(57) ABSTRACT

A hand-held biosensor including a housing having a lower handgrip portion and an upper target portion extending substantially perpendicular to the lower handgrip portion. An electromagnetic radiation emitter is received within the lower handgrip portion for emitting a laser beam toward a band pass filter received within the upper target portion. The band pass filter is configured to reflect the laser beam toward a target, and to permit passage therethrough of fluorescence emissions from the target. A photo-detector is received within the upper target portion of the housing and is configured to receive the fluorescence emissions from the target. A signal display is configured to provide an indication of fluorescence spectral data from the photo-detector. An adapter may be releasably coupled to the upper target portion of the housing for receiving atmospheric air.

19 Claims, 10 Drawing Sheets

(51) Int. Cl.
  G01N 21/31  (2006.01)
  G01N 21/39  (2006.01)
  G01N 21/17  (2006.01)
  G01N 30/00  (2006.01)

(52) U.S. Cl.
  CPC .  *G01N 2021/174* (2013.01); *G01N 2021/392* (2013.01); *G01N 2030/0095* (2013.01)

(56) References Cited

U.S. PATENT DOCUMENTS

| | | |
|---|---|---|
| 5,319,437 A | 6/1994 | Van Aken et al. |
| 5,435,307 A | 7/1995 | Friauf et al. |
| 6,255,118 B1 | 7/2001 | Alfano et al. |
| 6,407,395 B1 * | 6/2002 | Perov .................. G01N 21/6452 250/458.1 |
| 7,416,700 B2 | 8/2008 | Buechler et al. |
| 7,914,460 B2 | 3/2011 | Melker et al. |
| 8,211,035 B2 | 7/2012 | Melker et al. |
| 9,097,711 B2 | 8/2015 | Drader et al. |
| 9,140,648 B2 | 9/2015 | Tokhtuev et al. |
| 2006/0264761 A1 | 11/2006 | Knoche et al. |
| 2007/0224683 A1 * | 9/2007 | Clarke .................. G01N 21/65 436/46 |
| 2007/0232874 A1 * | 10/2007 | Ince ..................... A61B 5/0261 600/320 |
| 2009/0201490 A1 * | 8/2009 | Gerlitz ............... A61B 5/14532 356/39 |
| 2010/0021937 A1 | 1/2010 | Greenberg et al. |
| 2011/0117025 A1 | 5/2011 | Dacosta et al. |
| 2013/0006068 A1 | 1/2013 | Gemer et al. |
| 2015/0111287 A1 | 4/2015 | Rawle |

OTHER PUBLICATIONS

Chen et al., "Fluorescence measured using a field-portable laser fluorometer as a proxy for CDOM absorption", Estuarine, Coastal and Shelf Service, 146 (2014) 33-41, retrieved on Jun. 23, 2016 from http://soed.org.cn/en/upload/201503/d51e9fe07e0266c24a1d57550628c697.pdf.

Chekalyuk et al., "Advanced Laser Fluorometry of Natural Aquatic Environments", Limnology and Oceanography: Methods 6, 2008, 591-609, retrieved on Jun. 23, 2016 from http://onlinelibrary.wiley.com/doi/lom.2008.6.591.pdf.

* cited by examiner

HAND-HELD LASER BIOSENSOR

CROSS-REFERENCE TO RELATED APPLICATION

The present application claims priority to U.S. Provisional Patent Application Ser. No. 62/451,243, filed Jan. 27, 2017, the disclosure of which is expressly incorporated herein by reference.

STATEMENT REGARDING FEDERALLY SPONSORED RESEARCH OR DEVELOPMENT

The invention described herein includes contributions by one or more employees of the Department of the Navy made in performance of official duties and may be manufactured, used, and licensed by or for the United States Government without payment of any royalties thereon. This invention (Attorney Docket: 200,409) is assigned to the United States Government and is available for licensing for commercial purposes. Licensing and technical inquiries may be directed to the Technology Transfer Office, Naval Surface Warfare Center Corona Division, email: CRNA_CTO@navy.mil.

BACKGROUND AND SUMMARY OF THE DISCLOSURE

The present disclosure relates generally to methods and apparatuses for detecting and identifying chemicals in aerosol-particles and/or on surfaces. More particularly, the present invention relates to a hand-held laser based biosensor using "label-free" or native molecular fluorescence spectrophotometry for direct sampling of native biomolecules in solids, fluid, and/or atmospheric air.

While portable spectrophotometers are known to operate effectively on liquid samples, these devices encounter challenges when operating directly on atmospheric air or solids. Further, while laser molecular spectrophotometry has shown some success in remote sensing of atmospheric air or solids, challenges remain about safety concerns when laser beams are exposed to atmosphere, the useable wavelength of the lasers, and the lack of detection sensitivity.

As such, there remains a need for a portable biosensor for direct sampling on solids and/or atmospheric air, including particles, aerosols and spores, by using laser-based molecular fluorescence spectrophotometry.

According to an illustrative embodiment of the present disclosure, a hand-held biosensor includes an electromagnetic radiation emitter configured to emit a laser beam in a first direction along a first longitudinal axis, the laser beam having a wavelength of between 260 nm and 290 nm, which is used for excitation of amino acids tryptophan and tyrosine that are present in biomolecules. The hand-held biosensor further includes a first band pass filter configured to reflect the laser beam in a second direction along a second longitudinal axis substantially perpendicular to the first longitudinal axis toward a target, the first band pass filter configured to permit passage therethrough of fluorescence emissions from the target in a third direction along the second longitudinal axis opposite the second direction. A photo-detector is configured to receive the fluorescence emissions, and a processor is in electrical communication with the photo-detector to receive fluorescence spectral data from the photo-detector. A signal display is in electrical communication with the processor and is configured to provide an indication of the fluorescence spectral data. A first power supply is an electrical communication with the electromagnetic radiation emitter.

According to another illustrative embodiment of the present disclosure, a hand-held biosensor includes a housing having a lower handgrip portion extending between a lower end and an upper end along a first longitudinal axis, and an upper target portion extending between proximal end and a distal end along a second longitudinal axis substantially perpendicular to the first longitudinal axis. An electromagnetic radiation emitter is received within the lower handgrip portion and is configured to emit a laser beam in a first direction along the first longitudinal axis, the laser beam having a wavelength of between 260 nm and 290 nm, which is used for excitation of amino acids tryptophan and tyrosine that are present in biomolecules of a target. A first band pass filter is configured to reflect the excitation laser beam in a second direction along the second longitudinal axis substantially perpendicular to the first longitudinal axis toward the target, the first band pass filter configured to permit passage therethrough of fluorescence emissions from the target in a third direction along the second longitudinal axis opposite the second direction. A photo-detector is received within the upper target portion of the housing and is configured to receive the fluorescence emissions. A processor is in electrical communication with the photo-detector and is configured to receive fluorescence spectral data from the photo-detector. A signal display is in electrical communication with the processor and is configured to provide an indication of the fluorescence spectral data. A first power supply is in electrical communication with the electromagnetic radiation emitter. An adapter is releasably coupled to the distal end of the upper target portion of the housing for collecting ambient air.

According to a further illustrative embodiment of the present disclosure, a hand-held biosensor includes a housing having a lower handgrip portion extending between a lower end and an upper end along a first longitudinal axis, and an upper target portion extending between a proximal end and distal end along a second longitudinal axis substantially perpendicular to the first longitudinal axis. An electromagnetic radiation emitter is received within the lower handgrip portion and is configured to emit a laser beam in a first direction along the first longitudinal axis, the laser beam having a wavelength of between 260 nm and 290 nm. A first band pass filter is configured to reflect the laser beam in a second direction along the second longitudinal axis substantially perpendicular to the first longitudinal axis toward a target, the first band pass filter configured to permit passage therethrough of fluorescence emissions from the target in a third direction along the second longitudinal axis opposite the second direction. A photo-detector is received within the upper target portion of the housing adjacent the proximal end and is configured to receive the fluorescence emissions. A second band pass filter is supported adjacent to the distal end of the upper target portion, the second band pass filter covering the spectral region of between approximately 250 nm and approximately 400 nm. At least one lens is received within the target portion of the housing and defines a focal length for the laser beam to engage the target, the target portion of the housing including a first portion telescopingly coupled to a second portion for moving the at least one lens and thereby adjusting the focal length. A processor is in electrical communication with the photo-detector to receive fluorescence spectral data from the photo-detector. A signal display is in electrical communication with the processor and is configured to provide an indication of the fluorescence spectral data. A first power supply is in electrical communication with the electromagnetic radiation emitter, and a second power supply is in electrical communication with the signal display. The second power supply includes a battery supported by the target portion of the housing, and the signal display includes a liquid crystal display supported by the target portion of the housing. An adapter is releasably coupled to the distal end of the upper target portion of the housing for collecting ambient air.

Additional features and advantages of the present invention will become apparent to those skilled in the art upon consideration of the following detailed description of the illustrative embodiments exemplifying the best modes of carrying out the invention as presently perceived.

BRIEF DESCRIPTION OF THE DRAWINGS

A detailed description of the drawings particularly refers to the accompanying figures, in which.

DETAILED DESCRIPTION OF THE DRAWINGS

Various embodiments of the invention described herein are not intended to be exhaustive or to limit the invention to precise forms disclosed. Rather, the embodiments selected for description have been chosen to enable one skilled in the art to practice the invention.

Figure 1:
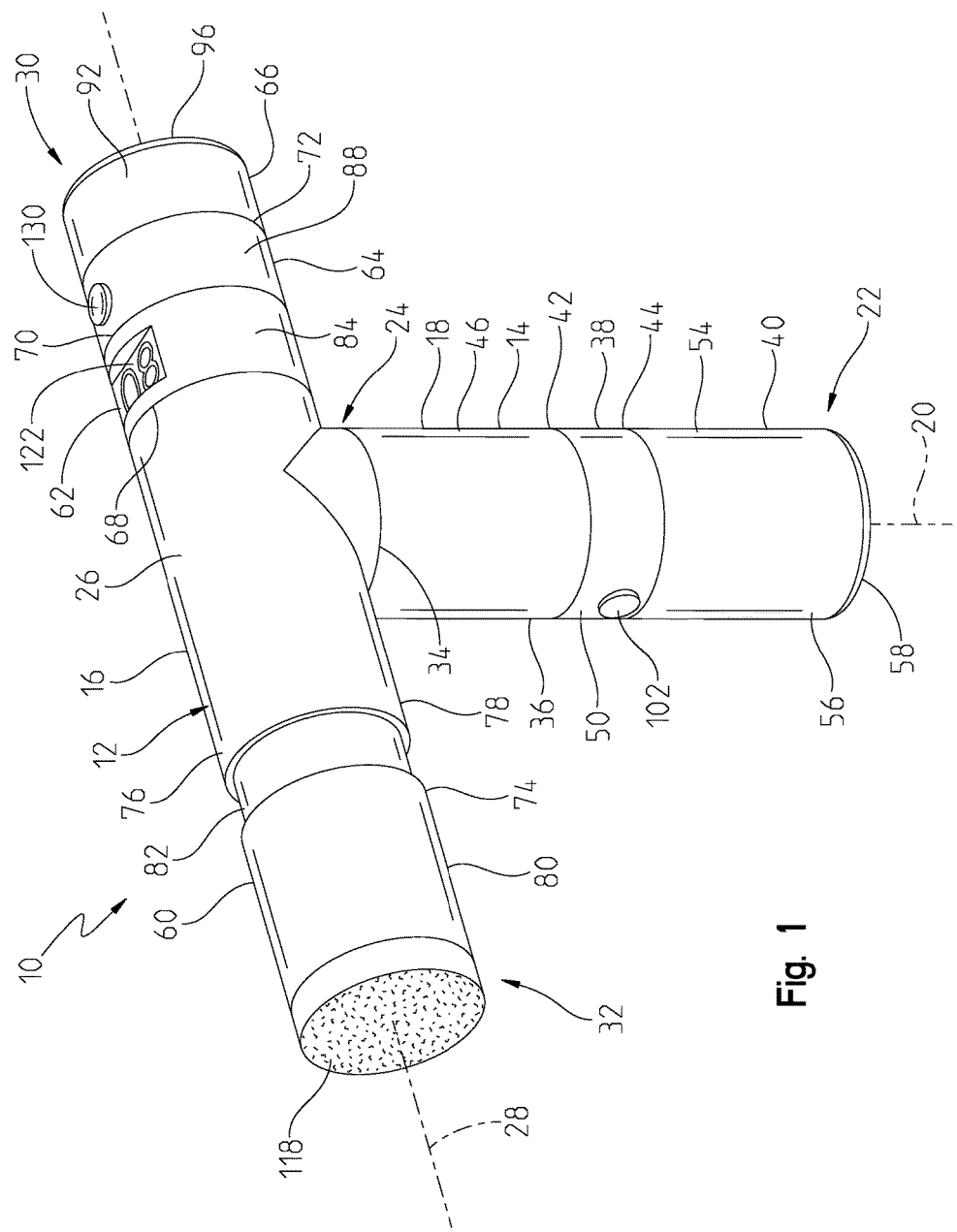
FIG. 1 is a perspective view of an illustrative hand-held laser biosensor of the present disclosure.

Referring initially to FIG. 1, an illustrative hand-held laser biosensor 10 is shown as including a housing or outer casing 12 having a lower handgrip portion 14 coupled to an upper target portion 16. The size and weight of the biosensor 10 are illustratively similar to those of a small hand-held hair blower. For example, the lower handgrip portion 14 may have a length of less than approximately 6 inches, the upper target portion 16 may have a length of less than approximately 10 inches, and the biosensor 10 may have a total weight of less than approximately 2 pounds.

The lower handgrip portion 14 illustratively includes a cylindrical sidewall 18 extending along a longitudinal axis 20 between a lower or proximal end 22 and an upper or distal end 24. Similarly, the upper target portion 16 illustratively includes a cylindrical sidewall 26 extending along a longitudinal axis 28 between a first or proximal end 30 and a second, distal or outlet end 32. Inner surfaces of the sidewalls 18 and 26 of the lower handgrip portion 14 and the upper target portion 16, respectively, are illustratively blackened to prevent light reflection. Illustratively, the lower handgrip portion 14 may be coupled to the upper target portion 16 by a releasable coupling 34, such as threads, a friction fit or a bayonet coupling.

The lower handgrip portion 14 may include a plurality of component sections or modules 36, 38 and 40 coupled together by releasable couplings 42 and 44, such as threads, friction fits or bayonet couplings. Illustratively, radiation emitter module 36 is operably coupled to control module 38 by releasable coupling 42, while power module 40 is operably coupled to the control module 38 by releasable coupling 44.

In an illustrative embodiment, the radiation emitter module 36 includes a radiation emitter module housing 46 having a cylindrical side wall 48, the control module 38 includes a control module housing 50 having a cylindrical side wall 52, and the power module 40 includes a power module housing 54 having a cylindrical side wall 56 and an end wall 58. The side walls 48, 52, 56 and end wall 58 are illustratively formed of a durable, light weight material, such as anodized aluminum or thermoplastic, and together define the lower hand grip portion 14 of the outer casing 12.

The upper target portion 16 may include a plurality of component sections or modules 60, 62, 64 and 66 coupled together by releasable couplings 68, 70 and 72, such as threads, friction fits or bayonet couplings. Illustratively, target module 60 is operably coupled to signal display module 62 by releasable coupling 68, control module 64 is operably coupled to the signal display module 62 by releasable coupling 70, and power module 66 is operably coupled to the control module 64 by releasable coupling 72.

The target module 60 illustratively includes a target module housing 74 including a cylindrical side wall 76 having a first, or proximal, portion or sleeve 78 and a second, or distal, portion or sleeve 80. The second sleeve 80 includes a reduced diameter portion 82 received within the first sleeve 78 in a telescoping manner. As such, the second sleeve 80, including the outlet end 32, is configured to move relative to the first sleeve 78 in an axial direction along the longitudinal axis 28.

The signal display module 62 illustratively includes a signal display module housing 84 having a cylindrical side wall 86. The control module 64 illustratively includes a control module housing 88 having a cylindrical side wall 90, and the power module 66 includes a power module housing 92 having a cylindrical side wall 94 and an end wall 96. The side walls 86, 90, 94 and the end wall 96 are illustratively formed of a durable, light weight material, such as anodized aluminum or thermoplastic, and together define the upper target portion 16 of the outer casing 12.

Figure 2:
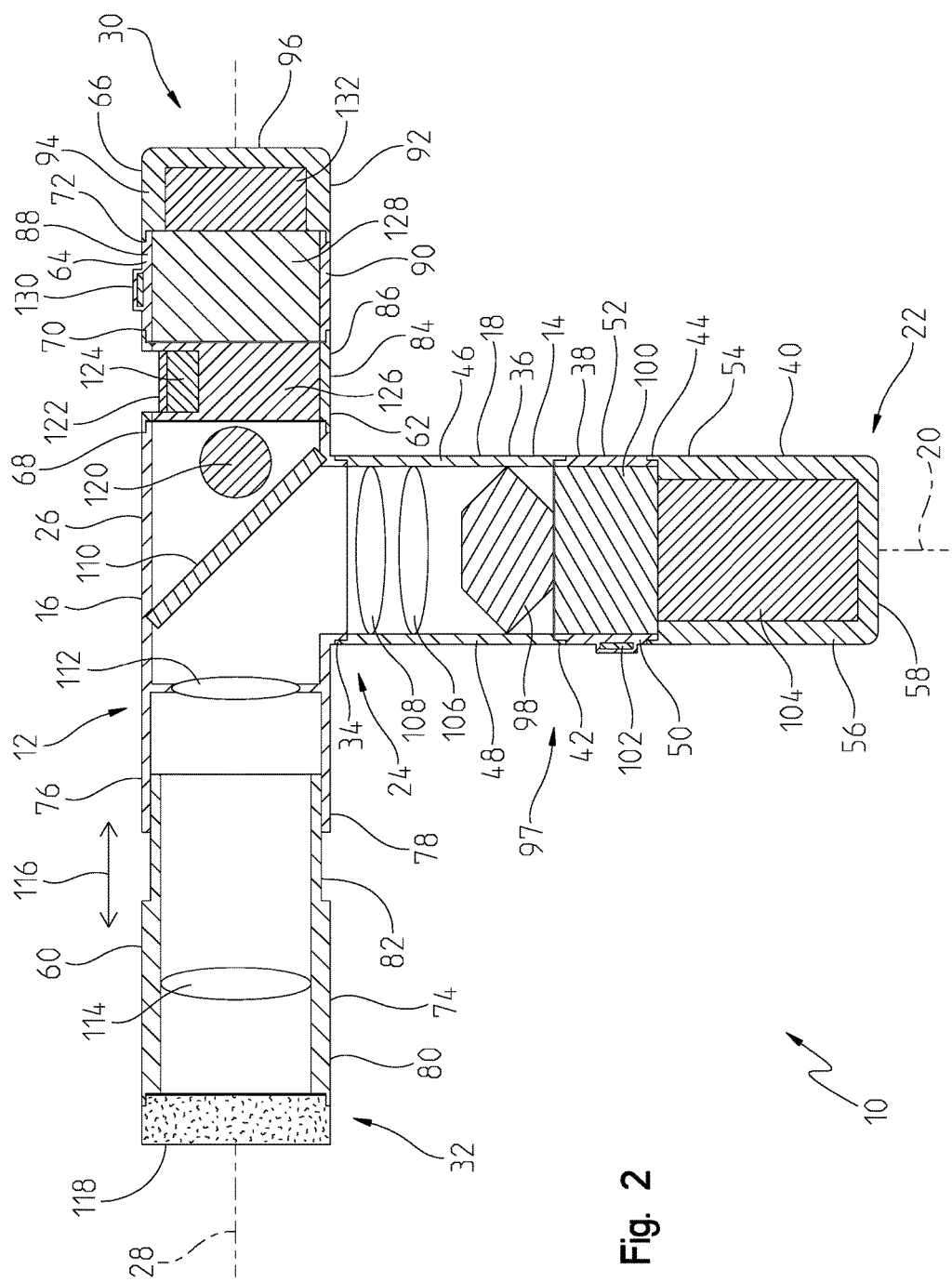
FIG. 2 is a cross-sectional view of the hand-held laser biosensor of FIG. 1.

With reference to FIG. 2, an electromagnetic radiation emitter or light source, illustratively a laser emitter 98 is illustratively supported within the radiation emitter module 36 of the lower handgrip portion 14. Illustratively, a driver 100 is operably coupled to laser emitter 98 and received within the control module 38. The laser emitter 98 is configured to emit electromagnetic radiation, illustratively in the form of a laser beam having a wavelength of between about 260 nm and 290 nm (e.g., centered at approximately 275 nm (+/−15 nm)), exciting amino-acids tryptophan and tyrosine in biomolecules, for native fluorescence. In the field of fluorescence spectroscopy, the higher the excitation (laser) power, the higher the fluorescence-emission-intensity from molecules impacted by the light from the laser emitter 98 (until quantum "saturation" is reached, at which point even higher laser power will achieve no gain in molecular emission).

Theoretically, all biomolecules include an amount of amino acids tryptophan and tyrosine. Spectrally, tryptophan and tyrosine uniquely absorb light-energy of approximately 275 nm wavelength, get excited and subsequently emit their characteristic fluorescence of approximately 345 nm wavelength. Operatively as a biosensor, the laser emitter 98 emits an electromagnetic radiation (e.g., laser beam) of approximately 275 nm wavelength that is directed and focused on a sample target 150; while a photo-detector 120 detects the collected light specifically of approximately 345 nm wavelength emitted from the sample target. A positive detection (signal above a baseline or background) from the biosensor 10 indicates sample target 150 contains biomolecules.

Illustratively, the laser emitter 98 comprises at least one laser diode. Currently available single laser diodes are capable of supplying a laser beam of about 20 mW (power) of 275 nm (wavelength). Illustratively, the laser emitter 98 comprises an array of several laser diodes defining a single "lamp". In one illustrative embodiment, five laser diodes may be provided, each emitting approximately 20 mW of power, for a total of about 100 mW. The number and type of laser diodes, along with individual and total laser power, may be optimized experimentally. For example, power levels of between 20 mW and 100 mW can be evaluated for different configurations. More particularly, higher laser powers are typically required for more distant targets (e.g., external to the biosensor 10 vs. internal to the biosensor 10). The driver 100 illustratively supplies a current level (usually about 200 mA) and generates a power from about 20 mW to about 100 mW.

Each laser diode may be of a type commercially available. For example, the laser diode may comprise a surface mount UV light emitting diode, 8-10 mW @ 275 nm (Part No. UVCLEAN275SMD), available from QPhotonics, LLC of Ann Arbor, Mich.

A power switch 102 is operably coupled to the laser driver 100. A first battery 104 is illustratively included within the power module housing 54. The power switch 102 may comprises a toggle push button that is configured to connect and disconnect power from the first battery 104 to the laser driver 100, and thereby activating and deactivating the laser emitter 98. Illustratively, for example, the "CW Laser Diode Drive LSC-025" available from Laser Components USA, Inc., may be used with a 9 V battery.

First and second lenses 106 and 108 are supported within the radiation emitter module 36 downstream from the laser emitter 98. The lenses 106 and 108 are configured to collimate the laser beam from the laser emitter 98 and focus the laser beam toward a first band pass filter 110. Illustratively, the lenses 106 and 108 are formed of a quartz material.

The first band pass filter 110 is illustratively supported within the target module 60 proximate to the intersection of the lower hand grip portion 14 and the upper target portion 16. The first band pass filter 110 allows passage therethrough of electromagnetic radiation within a certain wavelength range, and prevents passage therethrough of electromagnetic radiation at other wavelengths. In one illustrative embodiment, the first band pass filter 110 is illustratively a 345 nm band pass, 275 nm reflective filter. In other words, the illustrative filter 110 reflects a laser beam having a wavelength of about 275 nm, but allows passage therethrough of radiation having a wavelength of about 345 nm (e.g., molecular fluorescence from sample target 150).

More particularly, the laser beam emitted from the laser emitter 98 is directed in a distal direction along the longitudinal axis 20 to the first band pass filter 110. The laser beam is reflected by the first band pass filter 110 by approximately 90 degrees in a distal direction along the longitudinal axis 28 toward the outlet end 32 of the upper target portion 16. First and second lenses 112 and 114 are supported within the target module 60. The first lens 112 is supported by the first sleeve 78 of the target module housing 74, while the second lens 114 is supported by the second sleeve 80 of the target module 60.

A second band pass filter 118 is illustratively disposed at the outlet end 32 of the upper target portion 16. The filter 118 is illustratively a 250 nm-400 nm band pass filter. In other words, the illustrative second band pass filter 118 is configured to allow passage therethrough of radiation having a wavelength between about 275 nm and about 345 nm, while radiation having wavelengths outside of this range will be rejected (e.g., below about 250 nm and above about 400 nm).

Light is reflected from the target 150 (i.e., in a proximal direction along the longitudinal axis 28), through the second band pass filter 118 (if within the selected wavelength (e.g., between about 275 nm and about 345 nm) towards a photo-detector 120. The lenses 112 and 114 are illustratively of a quartz material, configured to collimate and focus the laser beam reflected from the first band pass filter 110 toward the target 150, and fluorescence from the target 150 toward the photo-detector 120. The lenses 112 and 114 are illustratively mounted on the adjustable sleeves 78 and 80, respectively, such that the distance therebetween may be adjusted. Illustratively, the lenses 106 and 108 are formed of a quartz material.

The photo-detector 120 may be a commercially available photo-detector, illustratively a silicon photodiode or silicon avalanche photodiode (Si APD). Illustratively, the photo-detector 120 may comprise a deep ultraviolet (DUV) detector such as a 5.7 (mm)$^2$ DUV photodiode with ceramic housing (Stock No. #84-982), or a 1.5 mm UV-VIS (200-1000 nm), Si APD detector (Stock No. #59-184), available from Edmund Optics of Barrington, N.J.

The signal display module housing 84 illustratively includes a display screen 122 coupled to a support, such as a printed circuit board 124. A fixing compound 126, such as an epoxy, may secure the display screen 122 and the printed circuit board 124 within the signal display module housing 84.

The display screen 122 is illustratively an electronic display configured to display digits (e.g., alphabetic and/or numeric characters), such as a light emitting diode (LED) display or a light crystal display (LCD). The photo-detector 120 emits electrical signals as current. The amplified current or current-to-voltage will be read digitally on the display screen 122. As an option, the display screen 122 can display an indication of positive or negative detection (e.g., "YES" or "NO") for a desired biomolecule within the target 150. As another option, the display screen 122 can show different colors or color-intensity-levels for positive detection within the target 150. Yet another option, the "display" is an audible device which gives alarm in the case for positive detection within the target 150.

The control module 64 illustratively includes a controller 128 received within the control module housing 88. The controller 128 may be operably coupled to the photo-detector 120 and the display screen 122. A power switch 130 is operably coupled to the controller 128. A second battery 132 is illustratively included within the power module housing 92. Illustratively, for example, a "Mini DC/DC High Voltage Module dBC-Series" commercially available from Laser Components USA, Inc. may be used as a part of controller 128 with a 3 or 5 V battery 132. The power switch 130 may comprises a toggle push button that is configured to connect and disconnect power from the second battery 132 to the controller 128, and thereby activate and deactivate the photo-detector 120 and the display screen 122.

Figure 3:
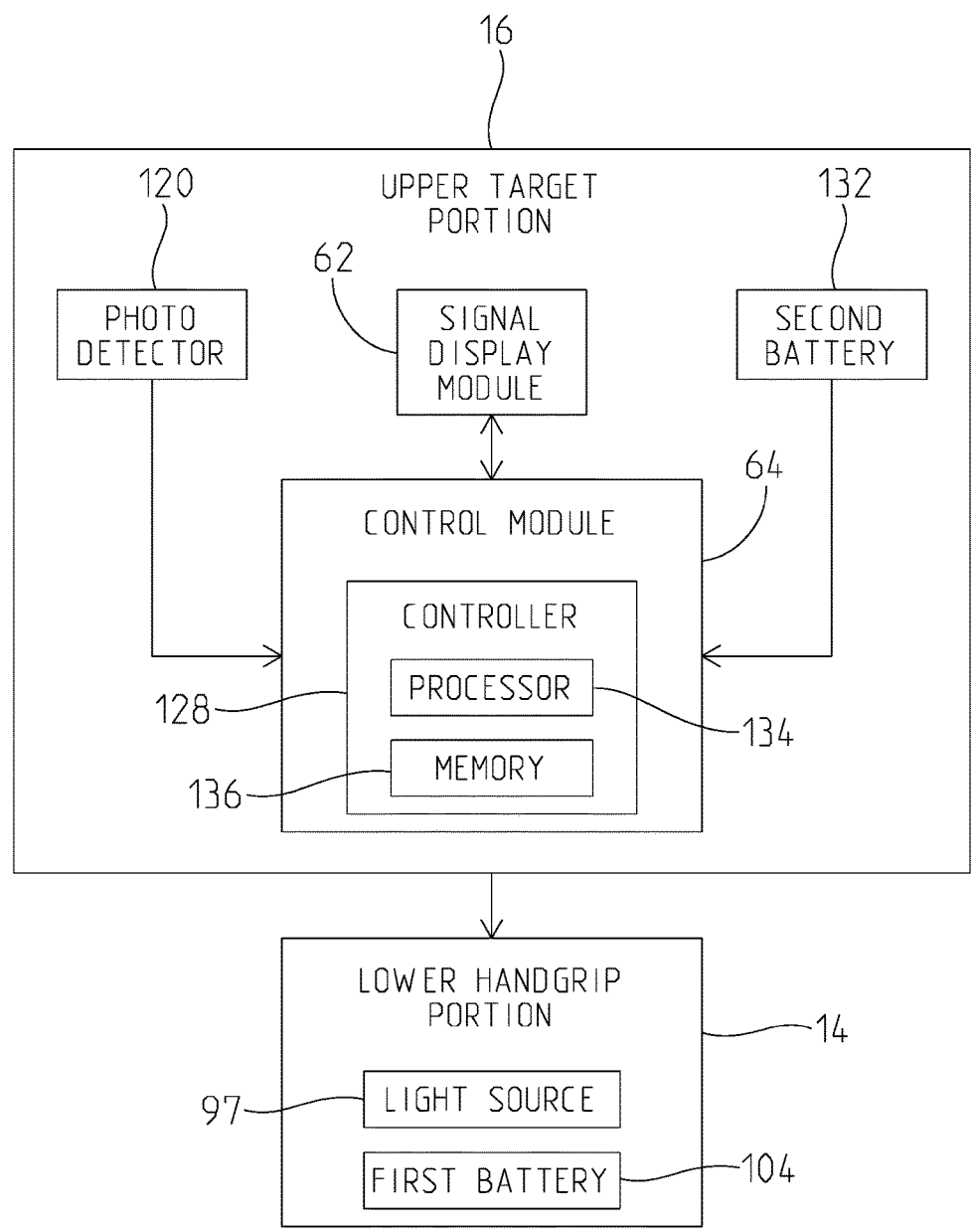
FIG. 3 is a block diagram illustrating interaction between various components of the hand-held laser biosensor of FIG. 1.

As shown in FIG. 3, the controller 128 may include a processor 134 operably coupled to a memory 136. The memory 136 may include software and/or firmware containing instructions executed by processor 134 for controlling the driver 100 and associated laser emitter 98, the photo-detector 120, the display screen 122, and/or other components of the biosensor 10. The memory 136 may include a random-access memory configured to store information, such as the date, the time and/or the number of positive hits. An electrical coupler, for example a communication port or transmitter (not shown), may be operably coupled to the controller 128 for providing electrical communication with the processor 134 to supply data to external devices, for example.

Figure 4:
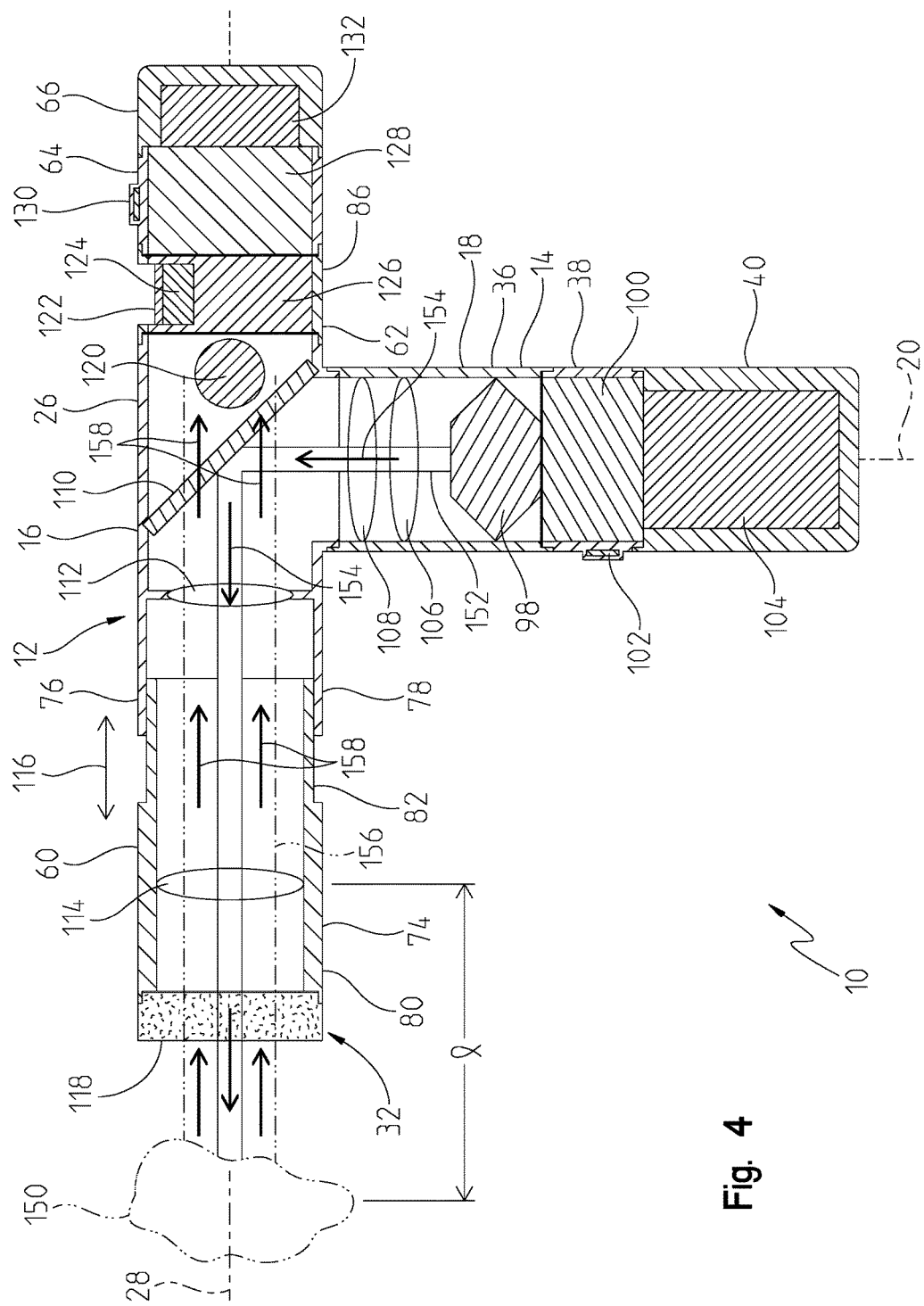
FIG. 4 is a cross-sectional view similar to FIG. 1, showing the biosensor in operation.

With reference now to FIG. 4, operation of the hand-held laser biosensor 10 illustratively begins with the user activating the laser driver 100 and the laser emitter 98 by depressing the activation button 102, and activating the photo-detector 120 and the display screen 122 by depressing the activation button 130. It should be appreciated that the activation button 102 and the activation button 130 could be combined into a single button configured to simultaneously activate the laser driver 100, the laser emitter 98, the photo-detector 120 and the display screen 122.

The excitation laser beam 152 emitted from the laser emitter 98 illustratively has a wavelength of between about 260 nm and 290 nm. The excitation laser beam 152 is reflected by the first band pass filter 110 at an angle (illustratively 90 degrees), and through the filter 118 toward the target 150 (as represented by arrows 154 in FIG. 4). The molecular fluorescence or emission 156 from the target 150 is directed axially in a proximal direction parallel to longitudinal axis 28 toward the photo-detector 120.

The photo-detector 120 supplies a signal regarding the biomolecule(s) detected in the target 150 by characteristics of the molecular fluorescence 156 (as represented by arrows 158). The processor 134 may retrieve characteristic data from the memory 136 and transmit a reading to the display screen 122. As an option, the display screen 122 can display a reading of positive or negative detection (e.g., "YES" or "NO") from the target 150. As another option, the display screen 122 can show positive detection from target 150 with readings of different colors or color-intensity-levels. As yet another option, the "display" is audible that sounds alarm in the case for positive detection within the target 150.

The display screen 122 may alternatively display a numerical reading of the molecular fluorescence 156. Illustratively, the intensity level of the display screen 122 is a digital scale from 0 to 100, with threshold readings representing safe, warning, and alarming detection from the target sample. Different colors displayed by the display screen 122 (e.g., backlighting) may indicate the detection result from the target-sample. For example, green may represent no detectable signal (i.e., safe), yellow may represent a low detection signal (i.e., warning), and red may represent a significant detection signal (i.e., alarming).

The biosensor 10 is illustratively a stand-alone unit whose operation is self-contained. However, other illustrative embodiments of the biosensor 10 may transmit information to remote units for analysis and/or storage. As such, the biosensor 10 may include a port for a wired connection and/or a transmitter for wireless transmission.

Figure 5:
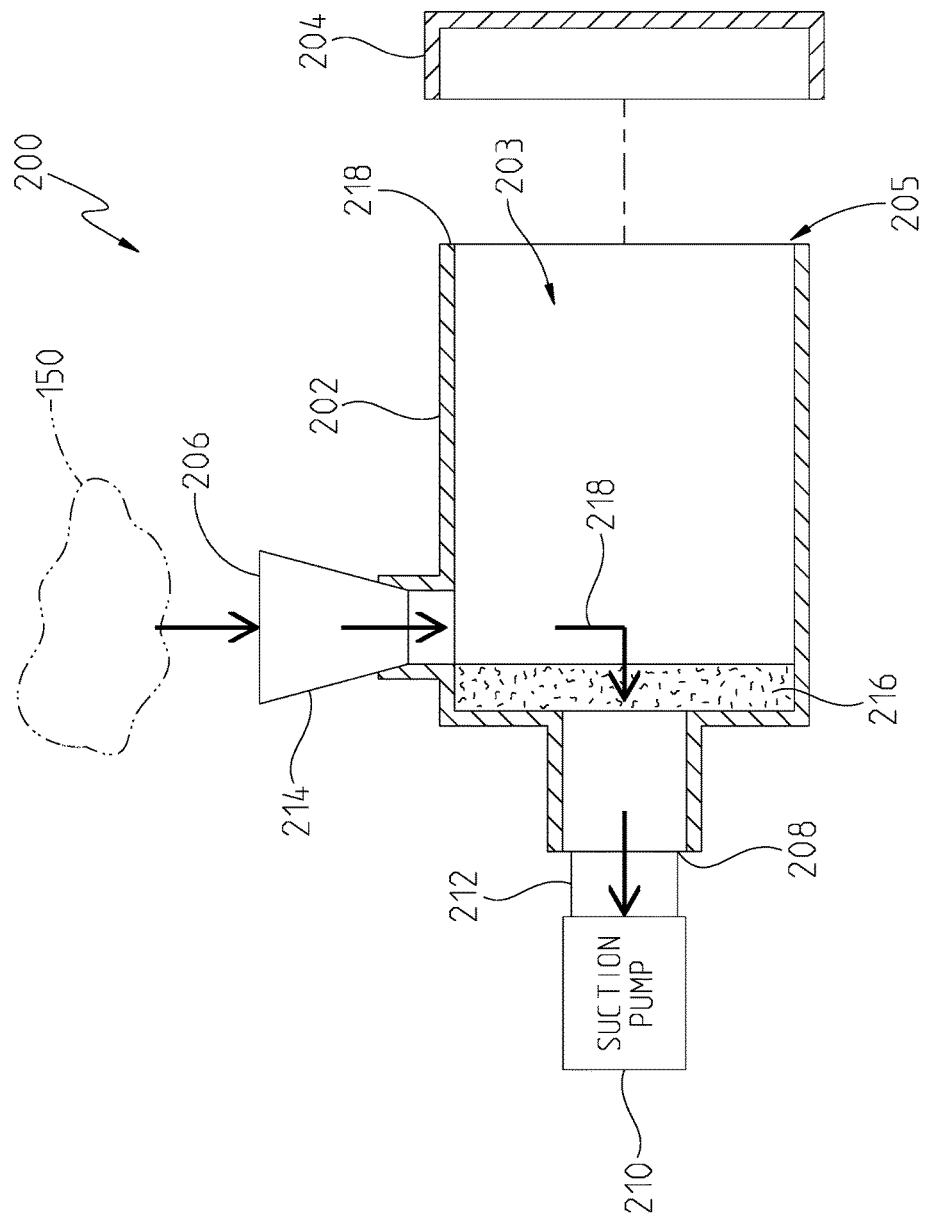
FIG. 5 is a cross-sectional view of an illustrative air sample concentrator.
Figure 6:
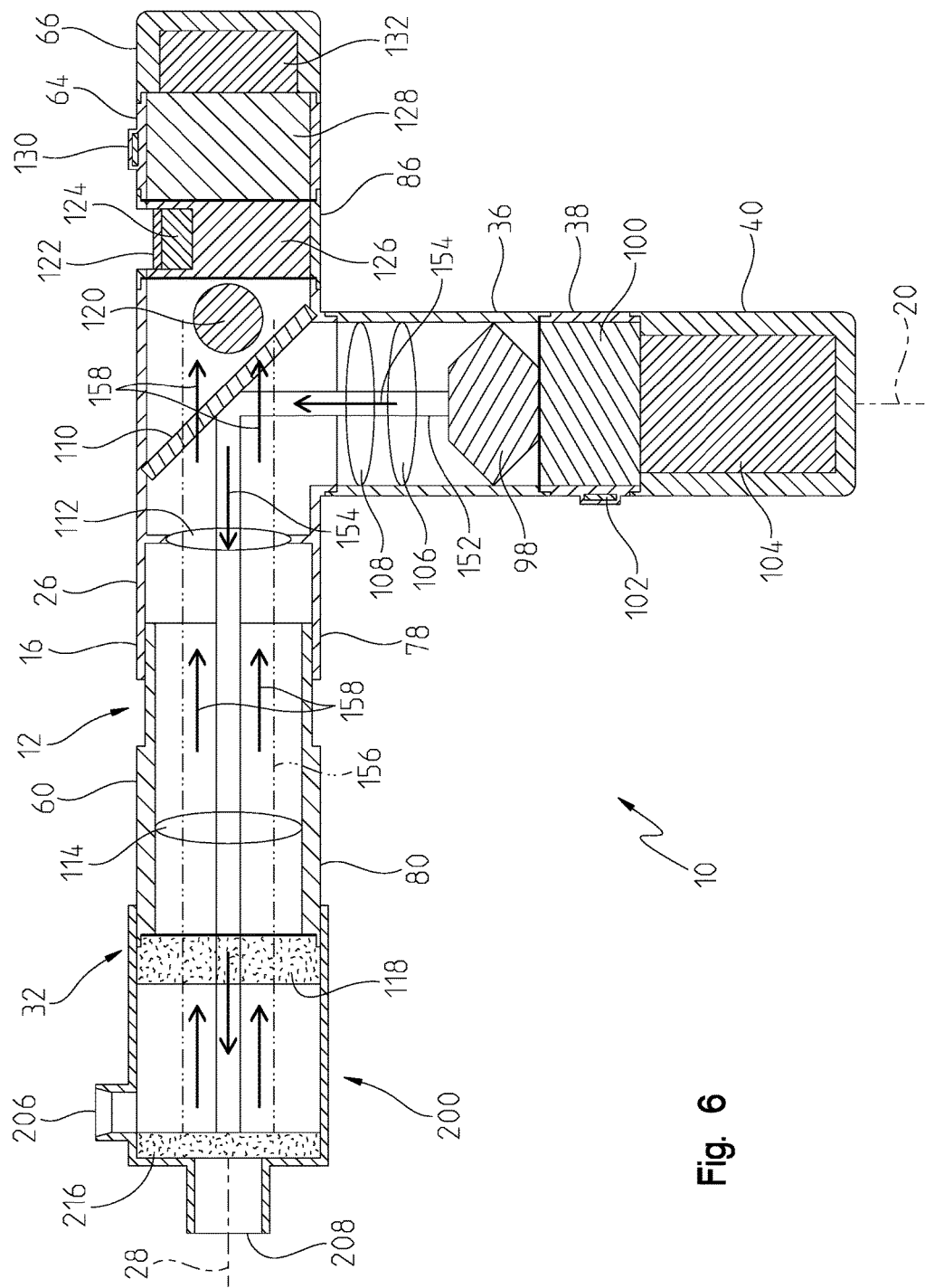
FIG. 6 is a cross-sectional view of the air concentrator of FIG. 5 coupled to the hand-held laser biosensor of FIG. 1, in an off-line mode of operation.
Figure 7:
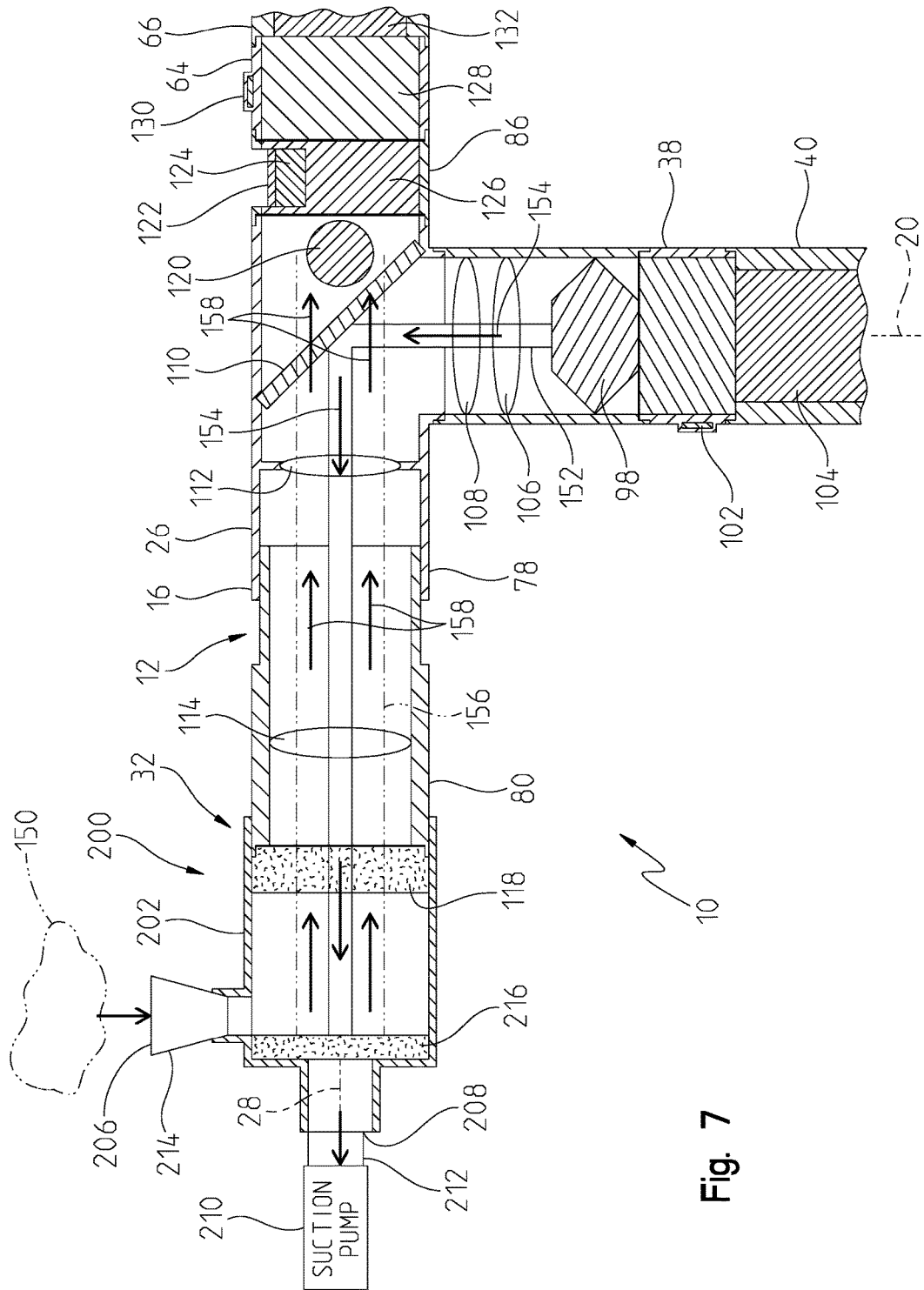
FIG. 7 is a cross-sectional view of the air concentrator of FIG. 5 coupled to the hand-held laser biosensor of FIG. 1, in an on-line mode of operation.

With reference now to FIGS. 5-7, an illustrative air sample concentrator 200 is shown for being releasably coupled to the outlet end 32 of the hand-held laser biosensor 10. The air sample concentrator 200 illustratively includes a cylindrical housing 202 defining a chamber 203, and a cap 204 configured to be releasably coupled to the housing 202 at a connection end 205. The housing 202 is illustratively formed of a durable material, such as aluminum, and includes a non-reflective (e.g., black colored) inner surface. The cap 204 may be coupled to the housing 202 using conventional releasable couplings, such as threads, a friction fit, or a bayonet coupling.

An air inlet 206 is configured to receive the air sample 150, and an air outlet 208 is configured to be fluidly coupled to a suction pump 210 through a conduit or tube 212. The shape and dimensions of the air inlet 206 and the air outlet 208 may be optimized experimentally. In one illustrative embodiment, the air inlet 206 is a funnel 214. More particularly, air is drawn into the housing 202 through a concentrator or filter 216, and out through the outlet 208 (as shown by arrows 218 in FIG. 5).

The suction pump 210 is illustratively a commercially available portable, light-weight vacuum pump. Illustratively, the suction pump 210 is configured to provide a suction rate of up to five liters of air per minute. Illustrative suction pumps 210 may comprise the commercially available light-weight GilAir Plus Personal Air Sampling Pump (1-5,000 cc/min) (http://www.sensidyne.com/), or the Gilian 5000 Personal Air Sampling Pump (20-5,000 cc/min).

The filter 216 is illustratively non-fluorescent on laser excitation at about 275 nm, for the detection region of interest, that is, about 345 nm, and is disposable after use. More particularly, the material of the filter 216 is selected such that, when it is illuminated with a laser beam of about 275 nm, it will not emit light that could interfere spectrally for the fluorescence detection around 345 nm, with a sample target collected (e.g., aerosols, spores, particles, airborne materials collected).

FIG. 6 is a cross-sectional view of the air sample concentrator 200 of FIG. 5 coupled to the hand-held laser biosensor 10 of FIG. 1 in an off-line mode of operation. In the off-line mode of operation, the concentrator 200 collects the target 150 externally, at a location of interest. For example, the air sample concentrator 200 is positioned externally of the biosensor 10 with the cap 204 coupled to the connection end 205 of the housing 202, and with the suction pump 210 coupled to the air outlet 208 via tube 212. The cap 204 is removed, and the connection end 205 of the housing 202 may be coupled to the outlet end 32 of the upper target portion 16 using conventional releasable couplings, such as threads, a friction fit, or a bayonet coupling.

The concentrating factor depends on the air suction rate and the length of time that the suction pump 210 is activated. After the air concentrating is complete, the air inlet 206 and the air outlet 208 are closed, and the air sample concentrator 200 is attached to the outlet end 32 of the biosensor 10 for laser excitation and fluorescence detection.

The working/optical distance may be adjusted to focus the laser beam 152 (as represented by arrows 154) on the filter 216. The laser light is enclosed during this operation to avoid accidental exposure. In other words, the laser radiation is enclosed within the outer casing 12 during the off-line mode of operation.

FIG. 7 is a cross-sectional view of the air concentrator 200 of FIG. 5 coupled to the hand-held laser biosensor 10 of FIG. 1 in an on-line mode of operation. Again, the connection end 205 of the housing 202 may be coupled to the outlet end 32 of the upper target portion 16 using conventional releasable couplings, such as threads, a friction fit, or a bayonet coupling. In the on-line mode of operation, the concentrator 200 remains attached to the biosensor 10. Illustratively, the filter 216 of the concentrator 200 collects the target 150 continually on-demand, through connection to the suction pump 210 via tubing 212. In other words, the suction pump 210 is continuously activated. The operator decides at what point in time the laser emitter 98 is activated for detection. For example, the laser emitter 98 could be activated after 30 seconds, and the corresponding fluorescence signal 156 (as represented by arrows 158) could be observed at the photo-detector 120. If the signal from the photo-detector 120 indicates a positive result, then use of a longer delay-activation-time will generate a higher signal due to the more sample-particles collected on the filter 216.

The working/optical distance may be adjusted to focus on the filter 216. For example, the distance between lenses 112 and 114 may be adjusted by moving sleeve 78 relative to sleeve 80 of the target module housing 74. The filter 216 is replaced for new operation. In this operation, the laser light is enclosed within the housings 12 and 202 to avoid accidental exposure.

Figure 8:
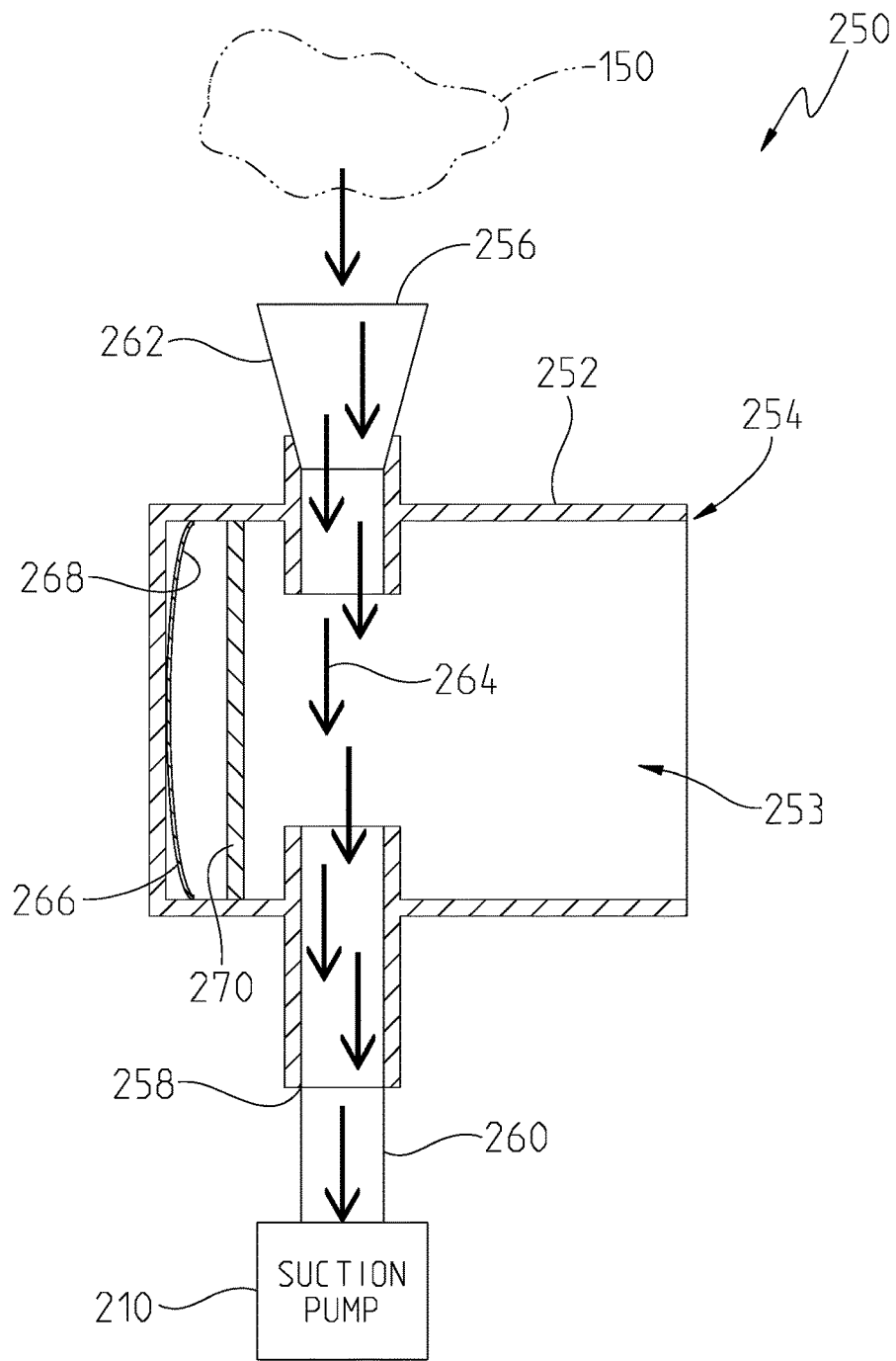
FIG. 8 is a cross-sectional view of an illustrative concave mirror continuous sample flow adaptor.
Figure 9:
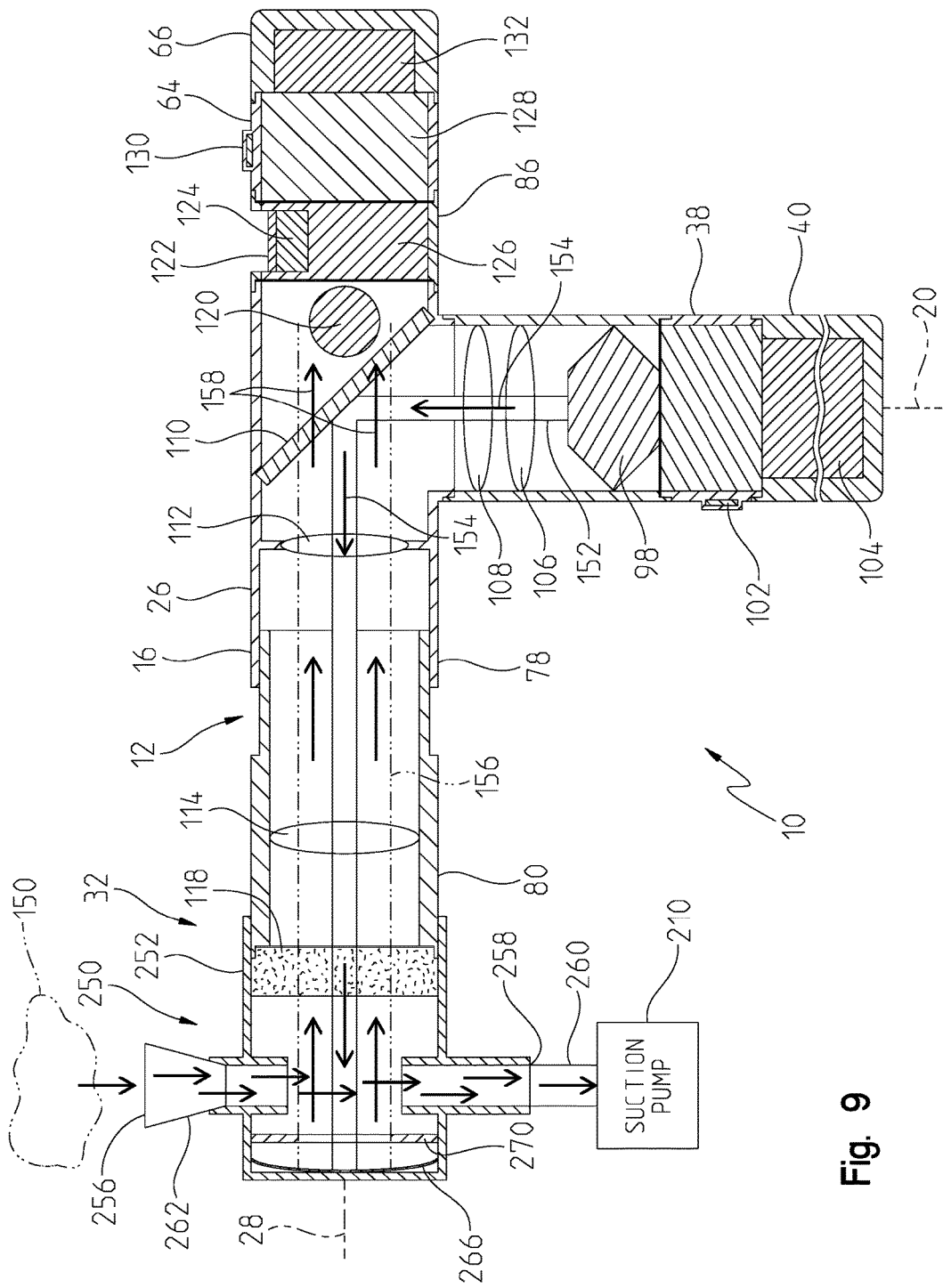
FIG. 9 is a cross-sectional view of the concave mirror continuous sample flow adaptor of FIG. 8 coupled to the hand-held laser biosensor of FIG. 1, in an on-line mode of operation.

FIGS. 8 and 9 show an illustrative concave mirror continuous sample flow adapter 250 for being releasably coupled to the outlet end 32 of the hand-held laser biosensor 10 of FIG. 1. The adapter 250 illustratively includes a housing 252 defining a chamber 253, and including a connection end 254. Illustratively, the connection end 254 of the housing 252 may be coupled to the outlet end 32 of the upper target portion 16 using conventional releasable couplings, such as threads, a friction fit, or a bayonet coupling. The housing 252 is illustratively formed of a durable material, such as aluminum, and includes a non-reflective (e.g., black colored) inner surface.

An air inlet 256 is configured to receive the target 150, and an air outlet 258 is configured to be fluidly coupled to suction pump 210 through a conduit or tube 260. The shape and dimensions of the air inlet 256 and the air outlet 258 may be optimized experimentally. In one illustrative embodiment, the air inlet 256 is defined by a funnel 262. More particularly, air is drawn into the housing 252, travels laterally through the housing 252 and out through the outlet 258 (as shown by arrows 264 in FIG. 8).

A concave mirror 266 includes a reflective surface 268. The concave mirror 266 is configured to increase light collection efficiency for both excitation (i.e., laser beam 152 with direction represented by arrows 154) from the laser emitter 98, and for fluorescence 156 (as represented by arrows 158) from biomolecules in the target 150, at flowing air 264. The reflective surface 268 may comprise a coating selected for best reflection in the required wavelength region/band covering the laser excitation and emission from the sample(s). More particularly, the reflective concave mirror 266 is configured to focus on the flowing air 264, and is highly reflective to radiation having wavelengths between about 275 nm and 345 nm. An illustrative example mirror 266 is a fused-silica mirror coated with aluminum (overcoated) $MgF_2$ surface 268.

A protective plate 270 is positioned proximal of the mirror 266 for protecting the reflective surface 268 from contamination. An illustrative example plate 270 is an uncoated UV fused-silica plate that has at least a 90 percent transmission efficiency for both the excitation laser beam 152 (i.e., 275 nm wavelength) and the emission light 158 (e.g., 345 nm wavelength). The optical distance for directing the excitation laser beam 152 (as represented by arrows 154) toward the air flow 264 may be adjusted for achieving the greatest signal to the photo-detector 120. For example, the distance between lenses 112 and 114 may be adjusted by moving sleeve 78 relative to sleeve 80 of the target module housing 74. Air is continuously flowing/passing the optical (excitation/fluorescence) region proximate the mirror 266 during this operation. In this operation, the laser beam 152 is enclosed within the housings 12 and 252 to avoid accidental exposure.

Figure 10:
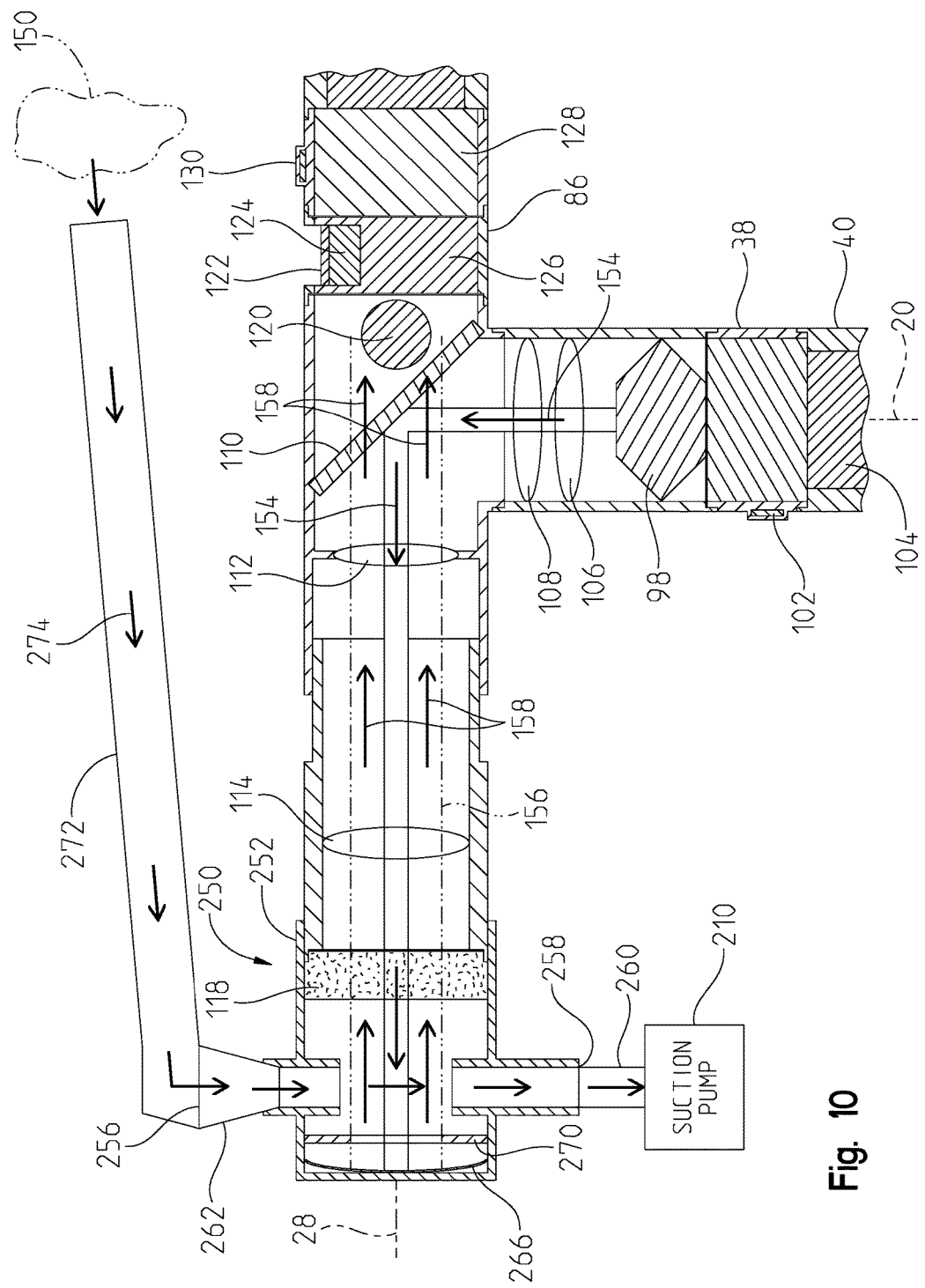
FIG. 10 is a cross-sectional view of the concave mirror continuous sample flow adaptor of FIG. 8 coupled to the hand-held laser biosensor of FIG. 1, configured for remote sampling of atmospheric air.

FIG. 10 illustrates the concave mirror continuous sample flow adapter 250 coupled to the hand-held laser biosensor 10 for remote sampling of atmospheric air (i.e., target 150). The connection end 254 of the housing 252 may be coupled to the outlet end 32 of the upper target portion 16 using conventional releasable couplings, such as threads, a friction fit, or a bayonet coupling. Remote sampling is achieved by using a sampling hose 272. The hose 272 is illustratively formed of a flexible, non-reactive material, such as a polymer, illustratively polytetrafluoroethylene, and has a length of several feet to several tens of feet. A longer hose 272 would require use of a stronger suction pump 210. The adapter 250 maintains a continuous air (sample) flow with choice of a light or heavy-duty suction pump 210. The signal display 122 is illustratively audible and sounds an alarm with positive detection from the photo-detector 120.

The optical distance for directing the excitation laser beam 154 toward the air flow 264 may be adjusted for achieving the greatest signal to the photo-detector 120. For example, the distance between lenses 112 and 114 may be adjusted by moving sleeve 78 relative to sleeve 80 of the target module housing 74. In this operation, the laser light is enclosed within the housings 12 and 252 to avoid accidental exposure.

There are many advantageous features of the illustrative biosensor 10 described in detail in this application. Such features include, for example, the label-free application for native fluorescence; the design, construction, and operation for direct-sampling, including the concentrating-adaptor for air-sample; the enclosed laser operation; the concave-mirror, continuous air-flow adaptor; the remote air-sampling hose; and, the small-size and light-weight of the biosensor 10.

Native fluorescence provides a major advantage for biomolecule-detection because all biomolecules contain amino acids (e.g., phenylalanine, tryptophan, and tyrosine), and, therefore, by laser excitation directly on original samples followed by positive fluorescence-detection indicates the present of (e.g., phenylalanine, tryptophan, and tyrosine) biomolecules. Characteristically, tryptophan and tyrosine absorb the laser 275 nm radiation, and when excited, emit their fluorescence radiation at 345 nm.

The simple operation is an advantage by push of a button 102, 130. The reliability on reading a result is an advantage by the signal displayed as digital number on the display screen 122. Yes/No, color/color-level, or an audible alarm/sound for positive detection, avoids the need for operator result interpretation. The short assay time is an advantage, an instance result is obtainable by pressing the buttons 102, 130 and reading the display screen 122. The enclosure of laser beam is an advantage that avoids potential exposure of invisible and damaging UV radiation during operation.

Although the invention has been described in detail with reference to certain preferred embodiments, variations and modifications exist within the spirit and scope of the invention as described and defined in the following claims.

The invention claimed is:

1. A hand-held biosensor comprising: an electromagnetic radiation emitter configured to emit a laser beam in a first direction along a first longitudinal axis, the laser beam having a wavelength between 260 nm and 290 nm; a first band pass filter configured to reflect the laser beam in a second direction along a second longitudinal axis substantially perpendicular to the first longitudinal axis toward a target, the first band pass filter configured to permit passage therethrough of fluorescence emissions from the target in a third direction along the second longitudinal axis opposite the second direction; a photo-detector configured to receive the fluorescence emissions; a processor in electrical communication with the photo-detector to receive fluorescence spectral data from the photo-detector; a signal display in electrical communication with the processor and configured to provide an indication of the fluorescence spectral data; and a first power supply in electrical communication with the electromagnetic radiation emitter; a housing including a lower handgrip portion extending between a lower end and an upper end along the first longitudinal axis, and an upper target portion extending between a proximal end and a distal end along the second longitudinal axis, the electromagnetic radiation emitter received within the lower handgrip portion, and the photo-detector received within the upper target portion an air sample concentrator configured to be coupled to the distal end of the upper target portion of the housing, the air sample concentrator including an inlet for receiving ambient air, an outlet for coupling to a suction pump, and a filter to collect air particles and biomolecules defining the target.

2. The hand-held biosensor of claim 1, wherein the electromagnetic radiation emitter comprises a laser diode array and a laser driver operably coupled to the laser diode array.

3. The hand-held biosensor of claim 1, further comprising at least one lens received within the target portion of the housing and defining a focal length for the laser beam to engage the target, the target portion of the housing including a first portion telescopingly coupled to a second portion for moving the at least one lens and thereby adjusting the focal length.

4. The hand-held biosensor of claim 1, further comprising a second band pass filter supported at the distal end of the upper target portion of the housing, the second band pass filter restricting passage to electromagnetic radiation having a wavelength of between approximately 250 nm and approximately 400 nm.

5. The hand-held biosensor of claim 1, further comprising a second power supply in electrical communication with the signal display, the second power supply including a battery supported by the target portion of the housing, and the signal display including a liquid crystal display supported by the target portion of the housing.

6. The hand-held biosensor of claim 1, wherein the filter is formed of a material that when impacted with a laser beam having a wavelength between approximately 260 nm and 290 nm, the filter will not interfere spectrally with fluorescence detection of approximately 345 nm wavelength.

7. The hand-held biosensor of claim 6, further comprising a sample concentrator coupled to the distal end of the upper target portion of the housing.

8. A hand-held biosensor comprising: a housing including a lower handgrip portion extending between a lower end and an upper end along a first longitudinal axis, and an upper target portion extending between a proximal end and a distal end along a second longitudinal axis substantially perpendicular to the first longitudinal axis; an electromagnetic radiation emitter received within the lower handgrip portion and configured to emit a laser beam in a first direction along the first longitudinal axis, the laser beam having a wavelength between 260 nm and 290 nm; a first band pass filter configured to reflect the laser beam in a second direction along the second longitudinal axis substantially perpendicular to the first longitudinal axis toward a target, the first band pass filter configured to permit passage therethrough of fluorescence emissions from the target in a third direction along the second longitudinal axis opposite the second direction; a photo-detector received within the upper target portion of the housing and configured to receive the fluorescence emissions; a processor in electrical communication with the photo-detector to receive fluorescence spectral data from the photo-detector; a signal display in electrical communication with the processor and configured to provide an indication of the fluorescence spectral data; a first power supply in electrical communication with the electromagnetic radiationemitter; and an adapter releasably coupled to the distal end of the upper target portion of the housing for collecting ambient air, wherein the adapter comprises an air sample concentrator configured to be coupled to the distal end of the upper target portion of the housing, the air sample concentrator including an inlet for receiving ambient air, an outlet for coupling to a suction pump, and a filter to collect air particles and biomolecules.

9. The hand-held biosensor of claim 8, wherein the electromagnetic radiation emitter comprises a laser diode array and a laser driver.

10. The hand-held biosensor of claim 8, further comprising at least one lens received within the target portion of the housing and defining a focal length for the laser beam to engage the target, the target portion of the housing including a first portion telescopingly coupled to a second portion for moving the at least one lens and thereby adjusting the focal length.

11. The hand-held biosensor of claim 8, further comprising a second band pass filter supported at the distal end of the upper target portion of the housing, the second band pass filter restricting passage to electromagnetic radiation having a wavelength of between approximately 250 nm and approximately 400 nm.

12. The hand-held biosensor of claim 8, further comprising a second power supply in electrical communication with the signal display, the second power supply including a battery supported by the target portion of the housing, and the signal display including a liquid crystal display supported by the target portion of the housing.

13. The hand-held biosensor of claim 8, wherein the filter is formed of a material that, when illuminated with a laser beam of approximately 275 nm wavelength, will not interfere spectrally with fluorescence detection of approximately 345 nm wavelength.

14. The hand-held biosensor of claim 8, wherein the adapter comprises a continuous sample flow adaptor configured to be coupled to the distal end of the upper target portion of the housing, the continuous sample flow adaptor including an inlet for receiving ambient air, an outlet for coupling to a suction pump, a protective fused silica-plate, and a concave mirror aligned with the second longitudinal axis.

15. A hand-held biosensor comprising: a housing including a lower handgrip portion extending between a lower end and an upper end along a first longitudinal axis, and an upper target portion extending between a proximal end and a distal end along a second longitudinal axis substantially perpendicular to the first longitudinal axis; an electromagnetic radiation emitter received within the lower handgrip portion and configured to emit a laser beam in a first direction along a first longitudinal axis, the laser beam having a wavelength between 260 nm and 290 nm; a first band pass filter configured to reflect the laser beam in a second direction along a second longitudinal axis substantially perpendicular to the first longitudinal axis toward a target, the first band pass filter configured to permit passage therethrough of fluorescence emissions from the target in a third direction along the second longitudinalaxis opposite the second direction; a photo-detector received within the upper target portion of the housing adjacent the proximal end and configured to receive the fluorescence emissions; a second band pass filter supported adjacent the distal end of the upper target portion, the second band pass filter covering the spectral region of between approximately 250 nm and approximately 400 nm; at least one lens received within the target portion of the housing and defining a focal length for the laser beam to engage the target, the target portion of the housing including a first portion telescopingly coupled to a second portion for moving the at least one lens and thereby adjusting the focal length; a processor in electrical communication with the photo-detector to receive fluorescence spectral data from the photo-detector; a signal display in electrical communication with the processor and configured to provide an indication of the fluorescence spectral data; a first power supply in electrical communication with the electromagnetic radiation emitter; a second power supply in electrical communication with the signal display, the second power supply including a battery supported by the target portion of the housing, and the signal display including a liquid crystal display supported by the target portion of the housing; and an adapter releasably coupled to the distal end of the upper target portion of the housing for collecting ambient air; a continuous flow air sample concentrator configured to be coupled to the distal end of the upper target portion of the housing, the continuous flow air sample concentrator including an inlet for receiving ambient air, an outlet for coupling to a suction pump, and a filter to collect air particles and biomolecules.

16. The hand-held biosensor of claim 15, wherein the filter is formed of a material that when illuminated with a laser beam of approximately 275 nm wavelength, it will not interfere spectrally with fluorescence detection of approximately 345 nmwavelength.

17. The hand-held biosensor of claim 15, further comprising of a sampling hose connected to the inlet of the continuous flow air sample concentrator for receiving ambient air.

18. A hand-held biosensor comprising:
a housing including a lower handgrip portion extending between a lower end and an upper end along a first longitudinal axis, and an upper target portion extending between a proximal end and a distal end along a second longitudinal axis substantially perpendicular to the first longitudinal axis;
an electromagnetic radiation emitter received within the lower handgrip portion and configured to emit a laser beam in a first direction along a first longitudinal axis, the laser beam having a wavelength between 260 nm and 290 nm;
a first band pass filter configured to reflect the laser beam in a second direction along a second longitudinal axis substantially perpendicular to the first longitudinal axis toward a target, the first band pass filter configured to permit passage therethrough of fluorescence emissions from the target in a third direction along the second longitudinal axis opposite the second direction;
a photo-detector received within the upper target portion of the housing adjacent the proximal end and configured to receive the fluorescence emissions;
a second band pass filter supported adjacent the distal end of the upper target portion, the second band pass filter covering the spectral region of between approximately 250 nm andapproximately 400 nm;
at least one lens received within the target portion of the housing and defining a focal length for the laser beam to engage the target, the target portion of the housing including a first portion telescopingly coupled to a second portion for moving the at least one lens and thereby adjusting the focal length;
a processor in electrical communication with the photo-detector to receive fluorescence spectral data from the photo-detector;
a signal display in electrical communication with the processor and configured to provide an indication of the fluorescence spectral data;
a first power supply in electrical communication with the electromagnetic radiation emitter;
a second power supply in electrical communication with the signal display, the second power supply including a battery supported by the target portion of the housing, and the signal display including a liquid crystal display supported by the target portion of the housing; and
an adapter releasably coupled to the distal end of the upper target portion of the housing for collecting ambient air
a continuous sample flow adaptor configured to be coupled to the distal end of the upper target portion of the housing, the continuous sample flow adaptor including an inlet for receiving ambient air, an outlet for coupling to a suction pump, and a concave mirror aligned with the second longitudinal axis.

19. The hand-held biosensor of claim 18, further comprising a sampling hose connected to the inlet of the continuous sample flow adaptor for receiving ambient air.

* * * * *